United States Patent [19]

Coan

[11] Patent Number: 4,697,003

[45] Date of Patent: Sep. 29, 1987

[54] METHOD OF PREPARING ALPHA-1-PROTEINASE INHIBITOR

[75] Inventor: Michael H. Coan, El Cerrito, Calif.

[73] Assignee: Miles Laboratories, Inc., Elkhart, Ind.

[21] Appl. No.: 793,807

[22] Filed: Nov. 1, 1985

[51] Int. Cl.$^4$ .............................................. C07G 7/00
[52] U.S. Cl. .................... 530/380; 530/416; 530/421; 530/424; 530/831; 424/101; 210/660; 210/670; 210/905; 210/927
[58] Field of Search .............. 424/101; 260/112 B, 260/112 R; 210/905, 927, 660, 670; 530/380, 416, 421, 424, 831

[56] References Cited

U.S. PATENT DOCUMENTS

| | | | |
|---|---|---|---|
| 3,415,804 | 12/1968 | Polson | 530/825 |
| 3,869,436 | 3/1975 | Falksveden | 424/101 |
| 4,100,149 | 7/1978 | Meiller et al. | 525/344 |
| 4,379,087 | 4/1983 | Coan et al. | 424/101 |

Primary Examiner—John Kight
Assistant Examiner—Nathan M. Nutter
Attorney, Agent, or Firm—Lester E. Johnson; Pamela A. Simonton

[57] ABSTRACT

There is disclosed a method for separating alpha-1-proteinase inhibitor (also known as alpha-1 antitrypsin) from an aqueous solution of plasma proteins, especially from Cohn Effluent II & III and Cohn Effluent I. The method includes the steps of first treating the aqueous solution to lower the concentration of salts therein and, optionally, its alcohol content, contacting the resulting solution with an anion exchange resin having selective affinity for alpha-1-proteinase inhibitor to selectively bind the alpha-1-proteinase inhibitor and allow unwanted plasma proteins to elute through the resin, displacing the alpha-1-proteinase inhibitor from the resin and recovering the same.

18 Claims, No Drawings

METHOD OF PREPARING ALPHA-1-PROTEINASE INHIBITOR

BACKGROUND OF THE INVENTION

1. Field of the Invention:

This invention relates to and has among its objects the provision of a novel method for separating alpha-1-proteinase inhibitor (PI) from blood plasma or blood plasma fractions. Further objects of the invention will be evident from the following description wherein parts and percentages are by weight unless otherwise specified.

2. Description of the Prior Art:

Alpha-1-proteinase inhibitor is a glycoprotein having molecular weight of 54,000. The protein consists of a single polypeptide chain to which several oligosaccharide units are covalently bound. Human PI has a role in controlling tissue destruction by endogenous serine proteinases. A genetic deficiency of PI, which accounts for 90% of the trypsin inhibitory capacity in blood plasma, has been shown to be associated with premature development of pulmonary emphysema. The degradation of elastin associated with emphysema probably results from a local imbalance of elastolytic enzymes and the naturally occurring tissue and plasma proteinase inhibitors. PI rapidly inhibits human pancreatic and leukocyte elastases (*Biochem. Biophys. Res. Comm.*, Vol. 72, No. 1, pages 33-39, 1976; ibid., Vol. 88, No. 2, pages 346-350, 1979).

A number of methods have been employed to isolate PI from the blood plasma. A majority of these methods are directed to laboratory scale isolation while others pertain to production on a commercial level.

Pannell et al., *Biochemistry*, Vol. 13, pages 5439-5445, (1974), employed a process wherein albumin-poor blood plasma was pooled and fractionated with solid ammonium sulfate (0.60-0.80 saturation). The precipitate resulting was solubilized and dialyzed and applied to a column of DEAE-cellulose. The fraction of PI eluting in the 0.05-0.15M NaCl linear gradient is pooled, concentrated, and dialyzed, and then applied again to a column of DEAE-cellulose. The PI fraction eluting in the linear gradient from 0.05-0.20M NaCl was collected, pooled, and concentrated to give PI.

In the method of Saklatvala et al., *Biochem. J.*, Vol. 157, pages 339-351 (1976), human plasma was fractionated using ammonium sulfate (80% saturation) to give a precipitate, which was dissolved, dialyzed and chromatographed on DEAE-cellulose. The 0.5M NaCl extract was applied to a concanavalin A-Sepharose column. The alpha-D-methyl glucopyranoside eluate was concentrated and applied again to a DEAE-cellulose column. The 0.0-0.2M NaCl eluate contained PI.

Fifty percent saturated ammonium sulfate precipitation was used by Musiani et al., *Biochem.*, Vol. 15, pages 798-804 (1976) to separate a PI-rich fraction that was solubilized and then subjected to successive chromatographic steps using DEAE ion exchanger, concanavalin A-Sepharose, Sephadex G-100, and an immunoadsorbent column to yield purified PI.

A large scale purification of PI from human plasma was disclosed by Kress et al., *Preparative Biochemistry*, Vol. 3, No. 6, pages 541-552 (1973). The precipitate from the 80% ammonium sulfate treatment of human plasma was dialyzed and chromatographed on DEAE-cellulose. The concentrate obtained was again dialyzed and gel filtered on Sephadex G-100. The PI-containing fractions were chromatographed twice on DE-52 cellulose to give PI.

Glaser et al., ibid., Vol. 5, No. 4, pages 333-348 (1975) isolated PI from Cohn Fraction IV-1 in 30% overall yield. Dissolved IV-1 was chromatographed on DEAE-cellulose, QAE-Sephadex, concanavalin A-Sepharose, and G-150 Sephadex to give PI.

An integrated plasma fractionation system based on polyethylene glycol (PEG) was disclosed by Hao et al., *Proceedings of the International Workshop on Technology for Protein Separation and Improvement of Blood Plasma Fractionation*, held Sept. 7-9, 1977, Reston, Va. In the published method Cohn cryoprecipitate was mixed with PEG in an amount of 40 grams per liter (g/l). All operations were conducted at 5° C.

After stirring for 60 minutes, the first fraction was removed by centrifugation. An additional 60 g/l of PEG was added to the supernate (final concentration approximately 10%). Prothrombin complex (PTC) was then extracted from the 10% PEG supernate by batchwise adsorption on DEAE cellulose, and an additional 100 g/l of PEG was added to obtain the 10-20% PEG precipitate. The four fractions thus obtained were 0-4% PEG precipitate, 4-10% PEG precipitate, 10-20% PEG precipitate and 20% PEG supernate, and were designated as Fractions A, B, C and D, respectively. It should be pointed out that these PEG concentrations were based on the original volume of cryosupernate.

The distribution of proteins in the four PEG fractions was as follows: Fibrinogen was the dominant protein in Fraction A with albumin being the major contaminant. Most of the contaminating albumin in Fractions A, B and C resulted from coprecipitation and/or entrapment of supernate since albumin by itself did not precipitate under these conditions. Fraction B was rich in plasminogen, C3 component of complement, IgG and IgM. In addition, virtually all of the beta-lipoproteins were present in this fraction. Fraction C contained appreciable quantities of alpha$_2$macroglobulin, IgA and was rich in prothrombin and other coagulation factors which constitute the so-called prothrombin complex. However, the authors found that better yields of PTC could be obtained from the 10% PEG supernate rather than from the 10-20% PEG precipitate. Fraction D was dominated by albumin but also contained all of the alpha-1-acid glycoprotein as well as most of the PI, antithrombin III (AT III), ceruloplasmin ($C_p$), haptoglobin, transferrin ($T_f$) and C1 esterase inhibitor (C1 inhib.). Several additional proteins were also isolated from Fraction D including prealbumin (PA), retinol binding protein (RBP), transcortin, and angiotensinogen. In general, most of the smaller proteins were in Fraction D.

Coan and Brockway, U.S. Pat. Nos. 4,379,087 and 4,439,358, disclose a method for separating alpha-1-proteinase inhibitor from a blood plasma fraction, e.g. Cohn Fraction IV-1, by providing an aqueous solution of the blood plasma fraction and holding such solution at a pH of about 6.5-8.5 and at a temperature of about 2°-50° C. for a period of about 0.2-24 hours, mixing the solution with an amount of polycondensed polyglycol, for example polyethylene glycol, in the range of about 8-10% to about 23% (wt./vol.), based on volume of solution, at a pH in the range of from about 4.6 to about 7.5 wherein the range of amount of polycondensed polyglycol increases about 2-3% per 0.5 increase in pH. In a preferred embodiment, there is used in the patented method about 10-15 g of polycondensed polyglycol per 100 ml of aqueous solution containing Cohn Fraction IV-1 at a pH in the range of 4.6–5.7, the ratio of parts of polycondensed polyglycol to parts of blood plasma fraction being from about 2:1 to 1:1. The alpha-1-proteinase inhibitor is separated from the resulting mixture by centrifuging the mixture from the polycondensed polyglycol treatment and recovering the supernatant solution, contacting the resulting supernatant solution with an anion exchange resin at a pH of about 5.5–8.6, and selectively eluting alpha-1-proteinase inhibitor from the resin. Alternatively, the alpha-1-proteinase inhibitor may be separated by the further addition of polycondensed polyglycol to precipitate alpha-1-proteinase inhibitor from the mixture following the initial centrifugation of the mixture.

SUMMARY OF THE INVENTION

The present invention is a new method for separating alpha-1-proteinase inhibitor (also known in the literature as "alpha-1 antitrypsin"), especially from sources not known heretofore and in a higher yield and purity than has been disclosed heretofore.

The invention described herein is a method for separating alpha-1-proteinase inhibitor from an aqueous solution of plasma proteins containing alpha-1-proteinase inhibitor which comprises the steps of:

(a) treating the aqueous solution to lower the concentration of salts therein by at least one means selected from diafiltration and gel filtration;

(b) contacting the solution obtained in step (a) above with an anion exchange resin having a selective affinity for alpha-1-proteinase inhibitor to selectively bind to the resin the alpha-1-proteinase inhibitor and to allow the plasma proteins which do not bind to the resin to elute through the resin into a first eluate;

(c) contacting the anion exchange resin having selectively bound thereto alpha-1-proteinase inhibitor obtained from step (b) with an eluant having sufficient ionic strength to displace the alpha-1-proteinase inhibitor from the resin into a second eluate; and (d) recovering alpha-1-proteinase inhibitor from the second eluate obtained from step (c).

The new source of alpha-1-proteinase inhibitor in the method according to the present invention is an aqueous solution of plasma proteins containing alpha-1-proteinase inhibitor selected from the group consisting of Cohn Effluent II+III, Cohn Effluent I, and cryosupernatant solution.

The primary advantage of the method according to the present invention is a higher recovery of PI, when compared with the yield of PI obtained by many methods reported in the prior art, in terms of yield from the total amount of PI in plasma.

Another advantage is the purity of the PI obtained by the method according to the present invention in that this method allows for enhanced separation of other plasma proteins which in prior art methods frequently are recovered along with PI as unwanted contaminants.

DESCRIPTION OF THE PREFERRED EMBODIMENTS

As mentioned above, the starting material for the method according to the present invention is an aqueous solution of plasma proteins containing alpha-1-proteinase inhibitor. Preferably, the aqueous solution containing PI is selected from the group consisting of Cohn Effluent II+III, Cohn Effluent I, and cryosupernatant solution. Cohn Effluent II+III and Cohn Effluent I may be obtained by fractionating blood plasma according to the Cohn ethanol fractionation technique or its modifications. See, for example, E. J. Cohn et al, *J. Amer. Chem. Soc.*, 68, 459 (1946); E. J. Cohn, U.S. Pat. No. 2,390,074; Oncley et al, *J. Amer. Chem. Soc.*, 71, 541 (1949); and "The Plasma Proteins", second edition, Volume III, pages 548–550, Academic Press, New York, N.Y. (1975). Cryosupernatant solution may be obtained by thawing fresh frozen plasma at not more than 5° C., removing the remaining precipitate (referred to as "cryoprecipitate") by conventional means, usually centrifugation, and retaining the supernatant solution ("cryosupernatant solution") for use in the method according to the present invention. See, for example, G. Mitra et al, U.S. Pat. No. 4,306,068. More preferably, the aqueous solution containing PI used as the starting material is selected from Cohn Effluent II+III and Cohn Effluent I. Most preferably, the starting aqueous solution containing PI is Cohn Effluent II+III.

As mentioned above, the first step in the method according to the present invention is to treat the starting aqueous solution of plasma proteins containing PI to lower the ionic strength of the solution, that is, to remove the salts in the aqueous solution, so that the PI will bind to the anion exchange resin. Preferably, the concentration of the salts in the starting aqueous solution should be about 0.02M or below, more preferably about 0.01M, and may be lowered by subjecting the aqueous solution to diafiltration or to gel filtration. Most preferably, the aqueous solution is subjected to diafiltration to lower the concentration of salts therein. Typcially, the starting aqueous solution is diafiltered in an Amicon ® cell using conventional techniques. Generally, the first step is carried out at a temperature of about 2°–10° C. and at a pH of about 6.0 to 7.0. Typical conditions are 5° C. and pH 6.5.

When the starting aqueous solution contains a plasma fraction obtained by the Cohn fractionation technique, that is Effluent II+III or Effluent I, preferably the solution is in an initial, additional step treated to concentrate it and to remove the alcohol contained in the solution by virtue of the use of the Cohn fractionation technique. A preferred technique to so concentrate the aqueous solution of Cohn Effluent II+III or Cohn Effluent I and to remove substantially all of the alcohol therein is to subject the aqueous solution to ultrafiltration. The conditions of temperature and pH in this ultrafiltration are generally the same as described for the above-described diafiltration wherein the ultrafiltration membrane is a Romicon ® PM-10 membrane.

The second step in the method according to the present invention is to contact the solution having lowered salt concentration, and optionally lowered alcohol concentration, with an anion exchange resin having selective affinity for the PI in the solution to selectively bind PI to the resin and to allow those plasma proteins which do not bind to the resin to elute through the resin into a first eluate. Although those plasma proteins which do not bind to the anion exchange resin are undesired as components in the composition containing PI, the first eluate generally is not discarded but, rather, is reworked to isolate plasma proteins having therapeutic or prophylactic uses other than those uses to which PI is directed. Although any anion exchange resin may be used, generally for use in the second step the anion exchange resin is a polysaccharide adsorbent selected from the group of polygalactose, polydextran, and cellulose resins wherein the polysaccharide chains have a positively charged group selected from diethylaminoethyl and quaternary ethyl groups attached ether linkages to the glucose units of the polysaccharide chains. Examples of suitable polysaccharide adsorbents useful as the anion exchange resin in this second step include commercially available resins such as DEAE-Sepharose, DEAE-Sephadex, DEAE-cellulose and QAE-Sephadex, and the like, available from Pharmacia Fine Chemicals, Piscataway, New Jersey. This step is generally carried out at about 2°–10° C. and pH 6.0–7.0, typically about 5° C. and pH 6.5. The concentration of the salts in the starting aqueous and wash solutions should be up to about 0.02M, preferably about 0.01M.

Although the solution from the first step may be contacted with the anion exchange resin by means of any suitable process such as, for example, a bulk process and a column chromatography process, the use of a column chromatography process is generally more convenient.

After the PI in the starting aqueous solution has been adsorbed from the solution by contact with and binding to the anion exchange resin and the other plasma proteins present in the solution have been eluted through the resin and the resin is washed using conventional techniques, then the anion exchange resin having selectively bound thereto alpha-1-proteinase inhibitor obtained from the second step, (b), is contacted with an eluant having sufficient ionic strength to displace the alpha-1-proteinase inhibitor from the resin into a second eluate. Broadly, the eluant having sufficient ionic strength to displace alpha-1-proteinase inhibitor from the anion exchange resin is an aqueous buffer solution containing at least one member selected from the group consisting of a water-soluble inorganic salt and a water-soluble organic salt having a concentration in the range of greater than about 0.02M to about 0.3M and having a pH in the range of about 5.5 to about 8.6. More preferably, the eluant used in the third step, (c), in the method according to the present invention is an aqueous solution of an inorganic salt. Most preferably, the eluant used in this step will have a concentration in the range of from about 0.02M to about 0.1M and the pH will be about 6.0 to about 7.0. Generally, the temperature during this step is about 2°–10° C., typically 5° C.

The final step in the method according to the present invention is to recover PI, in relatively high purity and yield, from the second eluate obtained in the third step as described above. This may be accomplished by any one of several means. Preferably, the technique useful to recover PI from the second eluate is by contacting the second eluate with a polycondensed polyalkylene glycol selected from polyethylene glycol (PEG) and polypropylene glycol (PPG). Although either may be used, PEG is preferred because it is more readily available, for example from Union Carbide Corp. The PEG may have a molecular weight in the range of about 200 to 20,000, preferably about 2,000–10,000, more preferably about 3,000 to 8,000, most preferably about 3,000 to 4,000.

Thus, the alpha-1-proteinase inhibitor may be recovered from the second eluate by (1) first contacting the second eluate with about 10% to about 20% (w/v), based on volume of second eluate, of the polycondensed polyalkylene glycol at a pH in the range of about 4.6 to 5.7 and at a temperature of about 2° C. to about 10° C. for a period of from about 1 minute to about 1 hour and separating the resulting precipitate and retaining the resulting supernatant solution, and (2) then contacting the retained supernatant solution with about 8% to about 15% (w/v), based on volume of second eluate, of additional polycondensed polyalkylene glycol at a pH in the range of about 4–6 to about 5.4 and at a temperature of about 2° C. to about 10° C. for a period of from about 1 minute to 1 hour and retaining the resulting precipitate which contains alpha-1-proteinase inhibitor.

Alternatively, in the place of contacting the above retained supernatant solution from the first polyalkylene glycol addition with additional polyalkylene glycol, the resulting retained supernatant solution or a solution of the resulting PI-containing precipitate reconstituted in buffer solution may be contacted with an anion exchange resin having an affinity for alpha-1-proteinase inhibitor, and then the alpha-1-proteinase inhibitor may be eluted from the anion exchange resin by contacting the resin with an eluant having sufficient ionic strength to displace the alpha-1-proteinase inhibitor to obtain a resulting third eluate which contains alpha-1-proteinase inhibitor. There may be used according to this alternative the anion exchange resins and the conditions described above in regards to adsorbing and eluting PI from the anion exchange resin in the second step, (b), according to the present invention.

Of course, the PI containing precipitate from the additional polyalkylene glycol precipitation may be dissolved in a suitable buffer solution which may then be subjected to the alternative anion exchange resin treatment.

Although the prior art discloses isolation of PI by treating plasma fractions including Cohn Fraction IV-1 and cryoprecipitate using conventional plasma protein precipitants and affinity chromatography techniques alone or in specific combinations, the method according to the present invention provides a means to obtain PI in high yield and purity from a source not heretofore known and from known sources as well.

Thus, a further aspect of the present invention is, in a method for separating alpha-1-proteinase inhibitor from an aqueous solution of plasma proteins containing alpha-1-proteinase inhibitor which comprises the steps of:
  (i) contacting an aqueous solution of a blood plasma fraction which contains alpha-1-proteinase inhibitor with from about 10% to about 35% (w/v), based on volume of aqueous solution, of polycondensed polyalkylene glycol, at a pH of about 4.6 to about 5.7 and at a temperature of about 2° C. to about 10° C. for a period of 1–24 hours to selectively precipitate unwanted proteins from the aqueous solution without precipitating alpha-1-proteinase inhibitor from the aqueous solution, and
  (ii) separating alpha-1-proteinase inhibitor from the solution obtained in step (i),
the improvement which comprises the prior steps of:
  (a) treating the aqueous solution of plasma proteins to concentrate the plasma proteins therein, to remove substantially all water-soluble plasma protein precipitant present in the starting aqueous solution, and to lower the ionic strength of the aqueous solution,
  (b) contacting the solution obtained in step (a) with an anion exchange resin having a selective affinity for alpha-1-proteinase inhibitor to selectively bind to the resin the alpha-1-proteinase inhibitor and to allow the plasma proteins which do not bind to the resin to elute through the resin into a first eluate; and (c) contacting the anion exchange resin having selectively bound thereto alpha-1-proteinase inhibitor obtained from step (b) with an eluant having sufficient ionic strength to displace the alpha-1-proteinase inhibitor from the resin into a second eluate, the second eluate comprising the aqueous solution treated according to the above steps (i) and (ii).

In the above described further aspect, the preferred starting aqueous solution of plasma proteins containing PI is selected from the group consisting of Cohn Effluent II+III and Cohn Effluent I. Also, the conditions for carrying out steps (a) and (b) are the same as described above for the same steps.

The PI obtained by the method according to the present invention, as a precipitate and reconstituted in buffer solution or as a solution or concentrate thereof, can be formulated into pharmaceutical preparations containing a protease inhibitory effective amount of PI and a pharmaceutically acceptable carrier for therapeutic, diagnostic, or other uses. To prepare them for intravenous administration the compositions are dissolved usually in water containing physiologically compatible substances such as sodium chloride, glycine, and the like and having a buffered pH compatible with physiological conditions. Generally, guidelines for intravenously administered compositions are established by governmental regulations. It is desirable that the PI concentrates be non-infective with respect to infectious microorganisms, e.g. hepatitis and AIDS viruses. In this respect the concentrates may be treated to inactivate such microorganisms and reduce infectivity to the same, for example, by one or more of sterile-filtration, ultraviolet irradiation, treatment with chemical viral inactivating agents, heat treatment (e.g. 60°-85° C.) in the lyophilized state, or "pasteurization", i.e., heating a PI-containing solution at a temperature and for a time, such as, for example, at about 60° C. or more for a period up to about 10 hours, sufficient to render the PI hepatitis non-infective. To stabilize the PI during this pasteurization, or "wet" heat treatment, a source of citrate ions is added in an amount sufficient to stabilize the PI during heating. Generally, if about 20 mg of total protein is present in the PI concentrate, then the solution is made about 0.25-0.5M in citrate ion. The pH of the mixture during this heating step should preferably be about 6.0-7.0.

To achieve maximum stabilization of PI during heating it is desirable to use a carbohydrate as the stabilization agent either alone or with sodium citrate. For this purpose one may use as the carbohydrate a mono-, di-, and trisaccharide such as arabinose, glucose, galactose, maltose, fructose, ribose, mannose, rhammose, sucrose, etc., or a sugar alcohol such as sorbitol and mannitol, etc., in an amount of about 0.5-2.4 g/ml of PI solution.

As mentioned above the pasteurized products of the invention may be incorporated into pharmaceutical preparations which may be used for therapeutic purposes. However, the term "pharmaceutical preparation" is intended in a broader sense herein to include preparations containing a protein composition in accordance with this invention used not only for therapeutic purposes, but also for reagent or diagnostic purposes as known in the art or for tissue culture. The pharmaceutical preparation intended for therapeutic use should contain a therapeutic amount of PI, i.e., that protease inhibitory amount necessary for preventative or curative health measures. If the pharmaceutical preparation is to be employed as a reagent or diagnostic, then it should contain reagent or diagnostic amounts of PI.

EXAMPLES

The invention described above is demonstrated further by the following illustrative examples.

Cohn Effluent II+III and Cohn Effluent I were obtained by means of fractionation according to the Cohn fractionation techniques mentioned above.

Assays

PI is estimated by its elastase inhibitory capacity, using a chromogenic substrate for elastase. Hydrolysis of N-succinyl-L-alanyl-L-alanyl-L-alanyl-p-nitroanilide ($SA_3pNA$) by elastase causes an increase in absorption at 405 nm. This increase is continuously monitored usually at 37° C. Comparisons of the linear changes of absorbance with time in the presence and absence of sample (PI) are made. The amount of inhibitor is then calculated based on the known molecular weights of elastase and PI, on the known 1:1 stoichiometry, and on the known amount of elastase used.

PI may also be estimated by its trypsin inhibitory capacity in a similar manner.

EXAMPLE 1

This example illustrates the first three steps, (a) lowering the concentration of salts of Cohn Effluent II+III solutions, (b) contacting the PI-containing solution from step (a) with an anion exchange resin, and (c) selectively eluting PI from the resin in the method according to this invention.

Cohn Effluent II+III was diafiltered against 5 volumes of 0.02M sodium phosphate buffer solution at pH 6.5 and at a temperature of 5° C.

Varying amounts of the diafiltered Cohn Effluent II+III set forth in Table I below were each applied to columns containing a constant amount of DEAE-Sepharose ® CL6B Fast Flow (Pharmacia Fine Chemical, Inc.) equilibrated with 0.02M sodium phosphate buffer solution at pH 6.5, 5° C. After the column was washed with one volume of 0.02M sodium phosphate buffer solution at pH 6.5, 5° C., the 0.02M sodium phosphate buffer eluate was discarded for other treatment.

Then the column was eluted with 0.05M sodium phosphate buffer solution at pH 6.5, 5° C. to displace the PI contained in the starting Cohn Effluent II+III that was bound to the DEAE-Sepharose ® CL6B resin.

Table I below summarizes the data from seven runs in the experiment described above. The amount of PI applied to the DEAE-Sepharose CL6B is expressed in terms of the absorbance of the sample at 280 mμ times the volume in ml per ml of DEAE. The percent yield of product is determined by multiplying by 100 the amount of PI in the second above-described eluate divided by the amount of PI in the starting Cohn Effluent II+III. The relative purity is the amount of inhibitor in the second above-described PI-containing eluate determined by the above-described assay procedure per total amount of protein in the eluate.

TABLE I

Results of Example 1

| Expt. | Amt. Diafiltrate Applied to DEAE Column ($A_{280}$ units/ml. DEAE) | % Yield (from Effl.) (II + III) | Relative Purity |
|---|---|---|---|
| 1-A | 383 | 16 | Not Assayed |
| 1-B | 293 | 42 | .15 |
| 1-C | 230 | 58 | .25 |
| 1-D | 209 | 49 | .16 |
| 1-E | 192 | 52 | .22 |
| 1-F | 185 | 37 | .28 |
| 1-G | 173 | 40 | .26 |

EXAMPLE 2

This example further illustrates variations for the first three steps in the method according to this invention, (a) lowering the ionic strength of Cohn Effluent II+III solutions, (b) contacting the PI-containing solution from step (a) with an anion exchange resin, and (c) selectively eluting PI from the resin.

In this example, a fixed amount of Cohn Effluent II+III, 230 $A_{280}$ units/ml DEAE, was applied to columns, containing a constant amount of DEAE-Sepharose CL6B, Fast Flow resin (100 g resin per 100 ml. buffer solution) equilibrated with 0.02M sodium phosphate buffer solution at pH 6.5, 5° C. After the column was washed with one volume of 0.02M sodium phosphate buffer solution at pH 6.5, 5° C., the 0.02N sodium phosphate buffer eluate was discarded for other treatment.

Then the column was eluted with 0.05M sodium phosphate buffer solution at pH 6.5, 5° C. to displace the PI contained in the starting Cohn Effluent II+III that bound to the DEAE-Sepharose CL6B resin.

Table II below summarizes the results of the experiment described above. The percent yield and relative purity were determined as described in Example 1.

TABLE II

Results of Example 2

| Expt. | Treatment Method | % Yield (from Eff.) (II + III) | Relative Purity |
|---|---|---|---|
| 2-A | Diafilter (DF) vs. 5 volumes 0.02 M sodium phosphate, pH 6.5 | 52 | .28 |
| 2-B | DF vs. 5 volumes $H_2O$ | 7.1 | .05 |
| 2-C | DF vs. 3 volumes $H_2O$ then 2 volumes 0.02 M phosphate | 9.8 | .16 |
| 2-D | Concentrate by ultra-filtration 2-fold, then DF vs 3 volumes 0.02 M phosphate | 3.0 | .08 |
| 2-E | Concentrate 2-fold, DF vs. 4 volumes phosphate | 53 | .25 |
| 2-F | Concentrate 2-fold, DF vs. 5 volumes phosphate | 49 | .32 |
| 2-G | Concentrate 3 fold, DF vs. 4 volumes phosphate | 44 | .21 |
| 2-H | Concentrate 3-fold, DF vs. 5 volumes phosphate | 65 | .30 |

EXAMPLE 3

This example illustrates the fourth step in the method according to the invention whereby PI was recovered from the eluate obtained in selectively displacing PI from the resin in the third step in the method according to the invention.

A pool of the eluate from step (c) obtained by eluting the DEAE-Sepharose CL6B column having PI bound thereto was divided into 6 equal portions. To each portion there was added PEG 3350 (Union Carbide Corp.) in sufficient quantity to provide 20% (w/v) of PEG in the solution. The pH was adjusted as described in Table III below, the temperature was held at 5° C., and the mixture agitated for about 1 hour and then centrifuged.

The clear supernatant solution was assayed for PI activity. The results of this experiment are summarized in Table III wherein the percent yield and relative purity were determined as described in Example 1.

TABLE III

Results of Example 3

| Expt. | pH Adjustment | % Yield of alpha-1-PI | Relative Purity |
|---|---|---|---|
| 3-A | pH 5.80 w/HCl | 75 | 0.48 |
| 3-B | pH 5.96 w/HCl | 87 | 0.46 |
| 3-C | pH 6.13 w/HCl | 84 | 0.36 |
| 3-D | pH 5.70 w/Acetic Acid | 65 | 0.49 |
| 3-E | pH 5.97 w/Acetic Acid | 81 | 0.46 |
| 3-F | pH 6.13 w/Acetic Acid | 83 | 0.32 |

EXAMPLE 4

This example illustrates the fourth step in the method according the present invention as in Example 3.

A pool of eluate from step (c) containing PI obtained as in Example 3 was divided into 6 equal portions and PEG 3350 was added to give 11.5% (w/v) based on original volume of DEAE-eluate. The pH and temperature were adjusted to pH 6.5 and 5° C., the mixture agitated for about 1 hour and then centrifuged. The clear supernatant solution was assayed for PI activity. The results of this experiment are summarized in Table IV wherein the percent yield and relative purity were determined as described in Example 1.

TABLE IV

Results of Example 4

| Expt. | pH Adjustment | % Yield of alpha-1-PI | Relative Purity |
|---|---|---|---|
| 4-A | pH 7.90 w/HCl | 56 | .46 |
| 4-B | pH 5.00 w/HCl | 60 | .42 |
| 4-C | pH 5.20 w/HCl | 73 | .42 |
| 4-D | pH 5.00 w/Acetic Acid | 68 | .46 |
| 4-E | pH 5.15 w/Acetic Acid | 76 | .47 |
| 4-F | pH 5.25 w/Acetic Acid | 82 | .47 |

EXAMPLE 5

This example illustrates the further purification of PI in the fourth step in the method according to the present invention.

A column eluate containing PI was obtained as described in Example 3 to give a PI-containing supernatant solution containing 20% (w/v) of PEG 3350 at a pH adjusted to 6.0. The supernatant solution was divided into 5 equal portions and to each portion there was added a further portion of PEG in the increments described in Table V below. PI precipitated from the PEG-containing supernatant solution. The PI was reconstituted in buffer solution and assayed for PI activity. The results of this experiment are described in Table V below wherein the percent yield was determined by multiplying by 100 the PI activity of the reconstituted solution divided by that of starting supernatant solution.

TABLE V

Results of Example 5

| Expt. | Additional PEG (% w/v) | % Yield alpha-1-PI |
|---|---|---|
| 5-A | 8 | 81 |
| 5-B | 10 | 97 |
| 5-C | 10 | 93 |
| 5-D | 12 | 100 |
| 5-E | 15 | 100 |

EXAMPLE 6

This example further illustrates the further purification of PI as described in Example 5 except that, in this example, two portions of column eluate obtained as described in Example 3 were assayed to determine the relative purity of PI in the column eluate. Then, the PI was separated from the column eluate by a 2-step PEG 3350 addition (20% plus 10%, w/v) as described in the above examples and the resulting PI precipitate was reconstituted in buffer solution and assayed for PI activity. The results are set forth in Table VI below.

TABLE VI

Results of Example 6

| Expt. | Relative Purity of Column Eluate | Relative Purity of Reconstituted Precipitate |
|---|---|---|
| 6-A | 0.25 | 0.53 |
| 6-B | 0.32 | 0.58 |

EXAMPLE 7

This example illustrates still further purification of PI obtained as described in Example 5 and 6 by chromatography on a DEAE-substituted polysaccharide resin, i.e. by DEAE anion exchange resin chromatography. The DEAE-Sepharose CL6B Fast Flow resin on a column (in duplicate) is equilibrated with 0.02M sodium phosphate buffer at pH 6.5 and the sample of PI-containing precipitate obtained according to Examples 5 and 6 reconstituted in buffer solution was applied to the column. After the column was washed with one volume of buffer solution, the PI that was bound to the anion exchange resin was eluted therefrom using 0.05M sodium phosphate buffer solutions pH 6.5. The results of this example are set forth in Table VII below.

TABLE VII

Results of Example 7

| Expt. | Relative Purify of Reconstituted Precipitate | Relative Purity of Column Eluate |
|---|---|---|
| 7-A | .58 | .75 |
| 7-B | .50 | .72 |

EXAMPLE 8

Substantially the same procedure as set forth in Example 1 was repeated except that Cohn Effluent I was substituted for Cohn Effluent II+III.

Cohn Effluent I was diafiltered against 5 volumes of 0.02M sodium phosphate buffer solution at pH 6.5 and at a temperature of 5° C.

The diafiltered Cohn Effluent I was applied to a column containing DEAE-Sepharose CL6B Fast Flow equilibrated with 0.02M sodium phosphate buffer solution at pH 6.5, 5° C. After the column was washed with one volume of 0.02M sodium phosphate buffer solution at pH 6.5, 5° C., the buffer eluate was discarded for other treatment.

Then, the column was eluted with 0.075M sodium phosphate buffer solution at pH 6.5, 5° C. to displace the PI contained in the starting Cohn Effluent I that was bound to the DEAE-Sepharose CL6B resin.

PI was recovered in the resulting eluate with a 30-fold purification with respect to the starting Cohn Effluent I.

What is claimed is:

1. A method for separating alpha-1-proteinase inhibitor from an aqueous solution of plasma proteins containing alpha-1-proteinase inhibitor selected from the group consisting of Cohn Effluent II+III, Cohn Effluent I and cryosupernatant solution which comprises the steps of:

(a) treating the aqueous solution to lower the concentration of salts therein to about 0.02M or below by at least one means selected from diafiltration and gel filtration;

(b) contacting the solution obtained from step (a) with an anion exchange resin having a selective affinity for the alpha-1-proteinase inhibitor in the solution to selectively bind to the resin the alpha-1-proteinase inhibitor and to allow the plasma proteins which do not bind to the resin to elute through the resin into a first eluate;

(c) contacting the anion exchange resin having selectively bound thereto alpha-1-proteinase inhibitor obtained from step (b) with an eluant having sufficient ionic strength to displace the alpha-1-proteinase inhibitor from the resin into a second eluate; and (d) recovering alpha-1-proteinase inhibitor from the second eluate obtained from step (c).

2. A method according to claim 1 wherein the aqueous solution of plasma proteins containing alpha-1-proteinase inhibitor is selected from the group consisting of Cohn Effluent II+III and Cohn Effluent I.

3. A method according to claim 1 wherein the aqueous solution of plasma proteins containing alpha-1-proteinase inhibitor is Cohn Effluent II+III.

4. A method according to claim 2 wherein prior to step (a), the aqueous solution is treated to remove substantially all of the alcohol present in the aqueous solution of the member of the group consisting of Cohn Effluent II+III and Cohn Effluent I.

5. A method according to claim 1 wherein in step (b) the anion exchange resin is a polysaccharide adsorbent selected from the group of polygalactose, polydextran, and cellulose resins wherein the polysaccharide chains have a positively charged group selected from diethylaminoethyl and quaternary ethyl groups attached by either linkages to the glucose units of the polysaccharide chains.

6. A method according to claim 1 wherein in step (c) the eluant having sufficient ionic strength to displace alpha-1-proteinase inhibitor from the anion exchange resin is an aqueous buffer solution containing at least one member selected from the group consisting of a water-soluble inorganic salt and a water-soluble organic salt having a concentration in the range of about 0.02M to about 0.3M and having a pH in the range of about 5.5 to about 8.6.

7. A method according to claim 1 wherein in step (d) the alpha-1-proteinase inhibitor is recovered from the second eluate by contacting the second eluate with a polycondensed polyalkylene glycol selected from polyethylene glycol and polypropylene glycol.

8. A method according to claim 7 wherein in step (d) the alpha-1-proteinase inhibitor is recovered from the second eluate by (1) first contacting the second eluate with about 10% to about 20% (w/v), based on volume of second eluate, of the polycondensed polyalkylene glycol at a pH in the range of about 4.6 to 5.7 and at a temperature of about 2° C. to about 10° C. for a period of from about 1 minute to about 1 hour and separating the resulting precipitate and retaining the resulting supernatant solution, and (2) then contacting the retained supernatant solution with about 8% to about 15% (w/v), based on volume of second eluate, of additional polycondensed polyalkylene glycol at a pH in the range of about 4.6 to about 5.4 and at a temperature of about 2° C. to about 10° C. for a period of from about 1 minute to 1 hour and retaining the resulting precipitate which contains alpha-1-proteinase inhibitor.

9. A method according to claim 8 including the additional steps of (3) reconstituting the resulting precipitate which contains alpha-1-proteinase inhibitor in buffer solution, (4) next contacting the solution from step (3) with an anion exchange resin having an affinity for alpha-1-proteinase inhibitor, and (5) then eluting the alpha-1-proteinase inhibitor from the anion exchange resin by contacting the resin with an eluant having sufficient ionic strength to displace the alpha-1-proteinase inhibitor to obtain a resulting third eluate which contains alpha-1-proteinase inhibitor.

10. A method according to claim 1 wherein in step (d) the alpha-1-proteinase inhibitor is recovered from the second eluate by (1) first contacting the second eluate with about 10% to about 20% (w/v) of a polycondensed polyalkylene glycol selected from polyethylene glycol and polypropylene glycol at a pH of about 4.6 to about 5.7 and at a temperature of about 2° C. to about 10° C. for a period of about 1 minute to 1 hour to precipitate unwanted proteins without precipitating alpha-1-proteinase inhibitor from the second eluate and separating the resulting precipitate and retaining the resulting supernatant solution, (2) next contacting the retained supernatant solution with an anion exchange resin having an affinity for alpha-1-proteinase inhibitor, and (3) then eluting the alpha-1-proteinase inhibitor from the anion exchange resin by contacting the resin with an eluant having sufficient ionic strength to displace the alpha-1-proteinase inhibitor to obtain a resulting third eluate which contains alpha-1-proteinase inhibitor.

11. A method according to claim 1 including the further step of treating the alpha-1-proteinase inhibitor obtained from step (d) to inactivate, and to reduce the infectivity of, infectious microorganisms so as to render the alpha-1-proteinase inhibitor non-infectious to such infectious microorganisms and thereby render the alpha-1-proteinase inhibitor useful for therapeutic and prophylactic purposes.

12. A pharmaceutical composition comprising a protease inhibitory effective amount of alpha-1-proteinase inhibitor produced by the method according to claim 1 and a pharmaceutically acceptable carrier.

13. A pharmaceutical composition comprising a protease inhibitory effective amount of alpha-1-proteinase inhibitor produced by the method according to claim 12 and a pharmaceutically acceptable carrier.

14. In a method for separating alpha-1-proteinase inhibitor from an aqueous solution of a blood plasma fraction containing alpha-1-proteinase inhibitor selected from the group consisting of Cohn Effluent II+III and Cohn Effluent I which comprises the steps of:
  (i) contacting the aqueous solution containing alpha-1-proteinase inhibitor with from about 10% to about 35% (w/v), based on volume of the aqueous solution, of a polycondensed polyalkylene glycol selected from polyethylene glycol and polypropylene glycol, at a pH of about 4.6 to about 5.7 and at a temperature of from about 2° C. to about 10° C. for a period of about 1-24 hours to selectively precipitate unwanted proteins from the solution without precipitating alpha-1-proteinase inhibitor, and
  (ii) separating alpha-1-proteinase inhibitor from the solution obtained in step (i),
the improvement which comprises the steps of:
  (a) treating the aqueous solution of the blood plasma fraction to remove substantially all of the alcohol present in the aqueous solution of the member of the group consisting of Cohn Effluent II+III and Cohn Effluent I;
  (b) treating the aqueous solution from step (a) to lower the concentration of salts therein to below about 0.02M by at least one means selected from diafiltration and gel filtration;
  (c) contacting the solution from step (b) with an anion exchange resin having a selective affinity for the alpha-1-proteinase inhibitor in the solution to selectively bind to the resin the alpha-1-proteinase inhibitor and to allow the proteins which do not bind to the resin to elute through the resin into a first eluate; and
  (d) contacting the anion exchange resin having selectively bound thereto alpha-1-proteinase inhibitor obtained from step (c) with an eluant having sufficient ionic strength to displace the alpha-1-proteinase inhibitor from the resin into a second eluate, which second eluate comprises the aqueous solution containing alpha-1-proteinase inhibitor treated according to the above steps (i) and (ii).

15. A method according to claim 14 wherein in step (c) the anion exchange resin is a polysaccharide adsorbent selected from the group of polygalactose, polydextran, and cellulose resins wherein the polysaccharide chains have a positively charged group selected from diethylaminoethyl and quaternary ethyl groups attached by ether linkages to the glucose units of the polysaccharide chains.

16. A method according to claim 14 wherein in step (d) the eluant having sufficient ionic strength to displace the alpha-1-proteinase inhibitor from the anion exchange resin is an aqueous buffer solution containing one of a water-soluble inorganic salt and a water-soluble organic salt having a concentration in the range of about 0.02M to about 0.3M and having a pH in the range of about 5.5 to about 8.6.

17. A method according to claim 14 including the further step of treating the alpha-1-proteinase inhibitor obtained from step (ii) to inactivate, and to reduce the infectivity of, infectious microorganisms so as to render the alpha-1-proteinase inhibitor non-infectious to such infectious microorganisms and thereby render the alpha-1-proteinase inhibitor useful for therapeutic and prophylactic purposes.

18. A pharmaceutical composition comprising a protease inhibitory effective amount of alpha-1-proteinase inhibitor produced by the method according to claim 14 and a pharmaceutically acceptable carrier.

* * * * *